United States Patent [19]

Henkelmann et al.

[11] Patent Number: 4,950,756
[45] Date of Patent: Aug. 21, 1990

[54] PREPARATION OF 1-NITROANTHRAQUINONE-2-CARBOXYLIC ACID

[75] Inventors: Jochem Henkelmann, Bensheim; Helmut Hoch, Weisenheim; Thomas-Michael Kahl, Roemerberg; Gerhard Kilpper, Carlsberg; Walter Maier, Ludwigshafen, all of Fed. Rep. of Germany

[73] Assignee: BASF Aktiengesellschaft, Ludwigshafen, Fed. Rep. of Germany

[21] Appl. No.: 429,143

[22] Filed: Oct. 30, 1989

[30] Foreign Application Priority Data

Nov. 30, 1988 [DE] Fed. Rep. of Germany ....... 3840341

[51] Int. Cl.$^5$ ................. C07C 265/30; C07C 207/00; C07C 50/24; C07C 97/24
[52] U.S. Cl. ................ 544/156; 546/204; 548/528; 552/251
[58] Field of Search .............. 552/251; 548/528; 544/156; 546/204

[56] References Cited

U.S. PATENT DOCUMENTS 1,540,467 6/1925 Fierz ...................... 552/251
3,211,754 10/1965 Klingsberg .................. 552/251

FOREIGN PATENT DOCUMENTS 1431961 4/1976 Fed. Rep. of Germany .
0618369 8/1978 U.S.S.R. ................. 552/251
7631 of 1910 United Kingdom .
7632 of 1910 United Kingdom .

OTHER PUBLICATIONS

Houben/Weyl, Methoden der Organischen Chemie, vol. VII/3c, pp. 255–257, (1979).

Primary Examiner—Richard L. Raymond
Assistant Examiner—Raymond Covington
Attorney, Agent, or Firm—John H. Shurtleff

[57] ABSTRACT

1-Nitroanthraquinone-2-carboxylic acid of the formula I

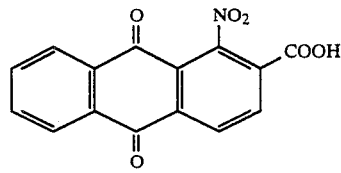

is prepared by treating novel 2-substituted 1-nitroanthraquinones of the general formula II

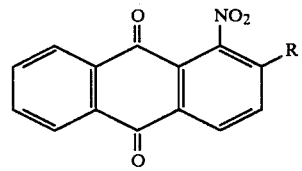

where R is —CH=CH—$R^1$ or —CH$_2$—CHO, where $R^1$ is $C_1$–$C_5$-dialkylamino or a cyclic 5- or 6-membered amine which may contain further hetero atoms, with oxidizing agents free of heavy metal.

3 Claims, No Drawings

PREPARATION OF 1-NITROANTHRAQUINONE-2-CARBOXYLIC ACID

The present invention relates to a new and improved process for preparing 1-nitroanthraquinone-2-carboxylic acid and to novel 2-substituted 1-nitroanthraquinones.

DE-A-2,242,643, DE-A-229,394 and Houben/Weyl, Methoden der Organischen Chemie, volume VII/3c, pages 255 to 257 (1979), disclose the preparation of 1-nitroanthraquinone-2-carboxylic acid by oxidation of 2-methyl-1-nitroanthraquinone with chromium(VI) salts in inorganic acids, which leaves large non-recyclable amounts of chromium(III) salts in the acid in question.

It is an object of the present invention to remedy the aforementioned disadvantages.

We have found that this object is achieved by a new and improved process for preparing 1-nitroanthraquinone-2-carboxylic acid of the formula I

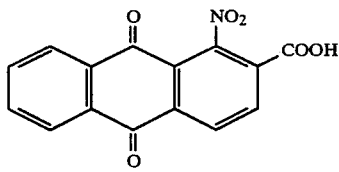

which comprises treating the novel 2-substituted 1-nitroanthraquinone of the general formula II

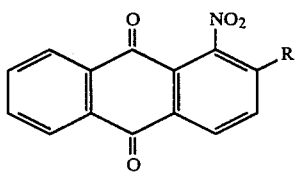

where R is —CH=CH—$R^1$ or —CH$_2$—CHO, where $R^1$ is $C_1$-$C_5$-dialkylamino or a cyclic 5- or 6-membered amine which may contain further hetero atoms, with an oxidizing agent free of heavy metal.

1-Nitroanthraquinone-2-carboxylic acid I is obtainable by the following methods:

It is prepared batchwise or continuously by reacting a 2-substituted 1-nitroanthraquinone II with an oxidizing agent free of heavy metal at elevated temperatures and pressures of from 1 to 50 bar, in the presence or absence of an initiator, in accordance with the following reaction equation:

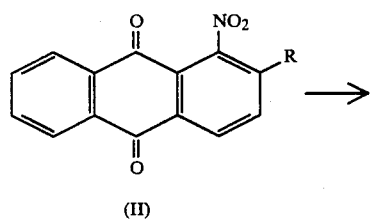

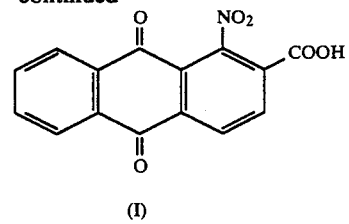

The reaction is in general carried out at from 40° to 200° C. and from 1 to 30 bar, preferably at from 50° to 150° C. and from 1 to 5 bar, particularly preferably at from 60° to 100° C. under atmospheric pressure.

Suitable oxidizing agents free of heavy metal are inorganic oxidizing agents, for example inorganic acids such as nitric acid or nitrous acid, organic acids such as peroxyformic acid, peroxyacetic acid, peroxytrifluoroacetic acid and m-chloroperoxybenzoic acid, peroxides such as $H_2O_2$ and alkyl hydroperoxides and inorganic salts, hypohalides such as sodium hypochloride. Particular preference is given to nitric acid and peroxyformic acid.

The molar ratio of oxidizing agent free of heavy metal: 2-substituted 1-nitroanthraquinone II is from 0.7:1 to 50:1, preferably from 0.95:1 to 20:1, particularly preferably from 1:1 to 10:1.

The oxidation with nitric acid may be carried out in the presence of an initiator. Suitable initiators are $NO_x$-liberating compounds, for example nitrites such as sodium nitrite, potassium nitrite, nitrous acid or nitrogen dioxide, and free radical initiators such as formaldehyde and hydroquinones, preference being given to sodium nitrite.

From 0.001 to 10 mol %, preferably from 0.01 to 5 mol %, particularly preferably from 0.05 to 2 mol %, of initiator are used per 2-substituted 1-nitroanthraquinone II. In general, the amount used is 0.1 mol %.

It is advisable, because of the strong exothermic nature of the reaction, not to convert a compound II where R is —CH=CH—$R^1$ directly into the carboxylic acid I but to convert it by hydrolysis with a non-oxidizing mineral acid into a compound II where R is —CH$_2$—CHO.

The hydrolysis is carried out at from 40° to 100° C., preferably at from 60° to 100° C., particularly preferably at from 80° to 100° C., under atmospheric pressure, but the reaction is also possible under reduced pressure and under superatmospheric pressure.

A non-oxidizing mineral acid is for example hydrochloric acid, hydrobromic acid, sulfuric acid or phosphoric acid, preference being given to hydrochloric acid and sulfuric acid, in particular to hydrochloric acid. In general, this non-oxidizing mineral acid is used in the form of a concentrated aqueous solution, but it is also possible to include an inert solvent, for example an alcohol such as methanol or ethanol, or a cyclic ether such as 1,4-dioxane or tetrahydrofuran.

The molar ratio of non-oxidizing mineral acid: compound II where R is —CH=CH—$R^1$ is from 0.9:1 to 50:1, preferably from 0.95:1 to 20:1, particularly preferably from 1:1 to 5:1.

The 2-substituted 1-nitroanthraquinones II where R is —CH=CH—$R^1$ are obtainable from 2-methyl-1-nitroanthraquinone III and a compound IV at elevated temperatures and pressures of from 1 to 50 bar according to the following reaction equation:

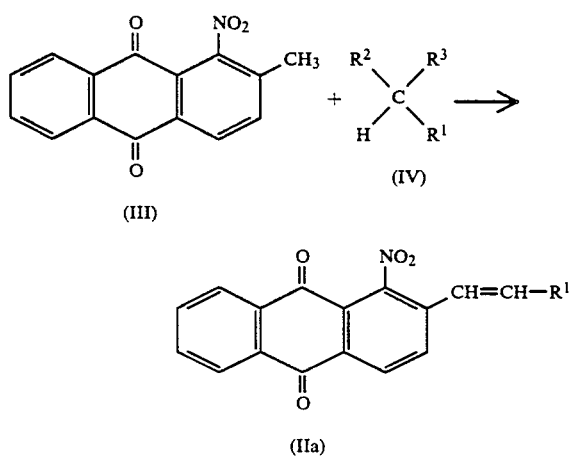

The reaction is in general carried out at from 60° to 160° C., preferably from 80° to 120° C., under pressures of from 1 to 5 bar, preferably from 1 to 2 bar, particularly preferably under atmospheric pressure.

The reaction can be carried out in the presence of an aromatic hydrocarbon such as toluene, a xylene, mesitylene, a chlorinated aromatic hydrocarbon such as chlorobenzene or a dichlorobenzene, cyclic ethers such as tetrahydrofuran or 1,4-dioxane, and formamide such as N,N-dimethylformamide or N,N-diethylformamide, or a cyclic urea such as N,N'-dimethylpropyleneurea or N,N'-dimethylethyleneurea, but it is particularly preferably carried out in N,N-dimethylformamide. It is also possible to use a solvent mixture.

The solvent quantity is freely choosable, but it is advisable to use from 50 to 500 ml per mol of III.

The molar ratio of IV:III is in general from 0.8:1 to 5:1, preferably from 1:1 to 2:1, particularly preferably from 1.1:1 to 1.5:1.

The compounds of the formula IV are partly known from Chem. Ber. 97 (1964), 3076–3080, and Chem. Ber. 101 (1968), 41–50, or can be obtained by the methods indicated therein.

The substituent R in the formula II is —CH═CH—$R^1$ or —CH$_2$—CHO.

The substituent $R^1$ in the formulae II and IV is $C_1$–$C_5$-dialkylamino, preferably $C_1$–$C_4$-dialkylamino, such as N,N-dimethylamino, N,N-diethylamino, N,N-diisopropylamino, or N,N-diisobutylamino, particularly preferably $C_1$–$C_2$-dialkylamino such as N,N-dimethylamino or N,N-diethylamino, or a cyclic 5- or 6-membered amine which may contain further hetero atoms such as nitrogen, oxygen or sulfur, such as N-pyrrolidino, N-piperidino or N-morpholino, preference being given to N-pyrrolidino and N-morpholino, with particular preference being given to N-pyrrolidino.

$R^2$ and $R^3$ in the formula III are each independently of the other $C_1$–$C_5$-alkoxy, preferably $C_1$–$C_4$-alkoxy, particularly preferably $C_1$–$C_2$-alkoxy such as methoxy or ethoxy, $C_1$–$C_5$-dialkylamino, preferably $C_1$–$C_4$-dialkylamino, particularly preferably $C_1$–$C_2$-dialkylamino such as dimethylamino, ethylmethylamino or diethylamino, or together are alkylenedioxy of 2 or 3 carbon atoms, such as —O—(CH$_2$)$_2$—O— or —O—(CH$_2$)$_3$—O—.

Particularly preferred compounds II are:
2-(2'-dimethylaminoethenyl)-1-nitroanthraquinone,
2-(2'-diethylaminoethenyl)-1-nitroanthraquinone,
2-(2'-N-pyrrolidinoethenyl)-1-nitroanthraquinone,
1-nitro-2-(2'-oxoethyl)-anthraquinone.

Particularly preferred compounds IV are:
N,N-dimethylaminodimethoxymethane
N,N-diethylaminodimethoxymethane
bis(N,N-dimethylamino)methoxymethane
tris(N,N-dimethylamino)methane
N-pyrrolidinodimethoxymethane 1-Nitroanthraquinone-2-carboxylic acid is inter alia an intermediate for vat dyes such as anthraquinoneazoles, acylaminoanthraquinones and phthaloylacridones (Ullmanns Encyklopädie der technischen Chemie, Verlag Chemie, Weinheim 1974, volume 7, pages 588, 590, 609–616, 631–635 and 638).

EXAMPLE 1

Preparation of 1-nitroanthraquinone-2-carboxylic acid by oxidation of 1-nitro-2-(2'-oxoethyl)anthraquinone with nitric acid 50 g (0.17 mol) of 1-nitro-2-(2'-oxoethyl)anthraquinone are suspended in 1000 g of 30–65% strength nitric acid. 10–20 mg of sodium nitrite are added, and the mixture is heated to 100° C. in the course of an hour. It is stirred at 70°–110° C. for 5–10 hours, cooled down to room temperature and filtered, and the yellowish brown powder is washed with water until neutral.

The crude product obtained is dissolved in 1000 ml of 5% strength aqueous sodium hydroxide solution, 25 g of sodium carbonate are added, and the solution is heated at 50°–80° C. for 2 hours. After filtration, the alkaline filtrate is acidified down to pH 2 with concentrated sulfuric acid (75% strength) and filtered, the filter residue is washed with water and dried. 1-nitroanthraquinone-2-carboxylic acid is obtained; melting point 284°–286° C. The results of a series of runs with various nitric acid concentrations are given in Table 1:

TABLE 1

| HNO$_3$ [% strength] | Time [h] | Temp. [°C.] | Yield [g] | Purity [%] | Yield of pure product [%] |
|---|---|---|---|---|---|
| 65 | 7 | 70–77 | 30.0 | 97 | 57 |
| 50 | 10 | 75 | 40.0 | 93 | 74 |
| 40 | 10 | 90–100 | 44.7 | 91 | 81 |
| 40 | 6.5 | 82–101 | 46.4 | 92 | 85 |
| 35 | 5 | 95–98 | 46.9 | 84 | 78 |
| 32.5 | 10 | 100–104 | 46.6 | 83 | 77 |

The crude product obtained can also be purified by recrystallization from ethanol or glacial acetic acid.

EXAMPLE 1a

Preparation of 1-nitro-2-(2'-oxoethyl)anthraquinone 100 g (0.31 mol) of 2-(2'-dimethylaminoethenyl)-1-nitroanthraquinone are refluxed with 200 g of concentrated hydrochloric acid (38% strength) and 600 g of water for 2 hours. After cooling, the precipitated crystals are filtered off, washed with water until neutral and dried at 70° C. This leaves 90.5 g (98.7%) of 1-nitro-2-(2'-oxoethyl)anthraquinone; melting point: 192° C.

EXAMPLE 2

Preparation of 1-nitroanthraquinone-2-carboxylic acid by oxidation of 2-(2'-dimethylaminoethyl)-1-nitroanthraquinone with nitric acid 50 g (0.16 mol) of 2-(2'-dimethylaminoethyl)-1-nitroanthraquinone are suspended in 50 g of concentrated nitric acid (65% strength) and 390 g of water, and the suspension is refluxed for 2 hours. After cooling down to room temperature, 500–1000 g of concentrated (65% strength) nitric acid and 10–20 mg of sodium nitrite are added, and the temperature is raised to 100° C. in the course of an hour. The mixture is stirred at 90°–100° C. for 7–10 hours, again cooled down to room temperature and filtered, and the pale brown powder is washed with water until neutral.

The crude product obtained is dissolved in 1000 ml of 5% strength sodium hydroxide solution, 25 g of sodium carbonate are added, and the solution is heated at 50°–80° C. for 2 hours. After filtration, the alkaline filtrate is acidified down to pH 2 with concentrated sulfuric acid (75% strength) and filtered, and the filter residue is washed with water and dried. 1-Nitroanthraquinone-2-carboxylic acid is obtained; melting point: 284°–286° C.

The results obtained with various amounts of nitric acid are given in Table 2:

TABLE 2

| Time [h] | HNO$_3$ 65% strength [g] | Yield [g] | Purity [%] | Yield of pure product [%] |
|---|---|---|---|---|
| 10 | 580 | 42 | 90 | 82 |
| 7 | 800 | 40 | 84 | 72 |
| 2 | 1000 | 40 | 80 | 69 |

The crude product obtained can also be purified by recrystallization from ethanol or glacial acetic acid.

EXAMPLE 2a

Preparation of 2-(2'-aminoethenyl)-1-nitroanthraquinones 267.0 g (1.0 mol) of 2-methyl-1-nitroanthraquinone and 1–2 mol of the corresponding aminodimethoxymethane in 1000 g of N,N-dimethylformamide are refluxed for 6–8 hours. The mixture is then distilled until a base of column temperature of 110° C. is reached. After cooling, the deep violet precipitate is filtered off with suction, washed with a little N,N-dimethylformamide and water and dried. The filtrate is concentrated and the residue is recrystallized from chlorobenzene, giving the results shown in Table 3.

TABLE 3

| 2-(2'-Aminoethenyl)-1-nitroanthraquinone | mp:[°C.] | Yield [%] |
|---|---|---|
| 2-(2'-dimethylaminoethenyl)-1-nitroanthraquinone | 268–272 dec. | 95 |
| 2-(2'-diethylaminoethenyl)-1-nitroanthraquinone | 235–241 dec. | 90 |
| 2-(2'-diisobutylaminoethenyl)-1-nitroanthraquinone | 177 | 87 |
| 1-nitro-2-(2'-N-pyrrolidino-ethenyl)anthraquinone | 235–239 dec. | 90 |

EXAMPLE 2b

Preparation of 2-(2'-diethylaminoethenyl)-1-nitroanthraquinone 42.0 g (0.16 mol) of 2-methyl-1-nitroanthraquinone (0.16 mol) and 46.2 g (0.32 mol) of diethylaminodimethoxymethane (0.32 mol) in 150 g of diethylformamide are refluxed for 7 hours. After all the volatiles have been distilled off, the residue is slurried in water and filtered with suction, and the filter residue is dried under reduced pressure. This gives 49.6 g (90.0%) of 2-(2'-diethylaminoethenyl)-1-nitroanthraquinone; melting point: 235°–241° C. (with decomposition).

EXAMPLE 3

Preparation of 1-nitroanthraquinone-2-carboxylic acid by oxidation of 2-(2'-dimethylaminoethenyl)-1-nitroanthraquinone with hydrogen peroxide in formic acid/acetic acid A solution of 10 g (0.031 mmol) of 2-(2'-dimethylaminoethenyl)-1-nitroanthraquinone in 100 ml of formic acid or acetic acid is admixed with from 5 to 15 times the molar amount of 30% strength hydrogen peroxide solution in water. After stirring for 2–10 hours the suspension formed is added to 200 ml of water, the mixture is filtered, and the filter residue is washed until neutral and dried. Purification is carried out as described in Example 2.

The results of using various reaction temperatures are shown in Table 4:

TABLE 4

| | T [°C.] | Time [h] | H$_2$O$_2$ | Yield [g] | Purity [%] | Yield of pure product [%] |
|---|---|---|---|---|---|---|
| Formic acid | 28° C. | 10 | 0.31 mol | 8.6 | 84 | 78 |
| Formic acid | 28–50° C. | 4 | 0.31 mol | 9.2 | 89 | 89 |
| Formic acid | 50° C. | 4 | 0.31 mol | 9.0 | 89 | 87 |
| Formic acid | 80° C. | 3 | 0.16 mol | 8.8 | 49 | 47 |
| Formic acid | 90° C. | 7 | 0.31 mol | 8.7 | 76 | 72 |
| Acetic acid | 50° C. | 6 | 0.31 mol | 9.0 | 71 | 69 |

We claim:

1. A process for preparing 1-nitroanthraquinone-2-carboxylic acid of the formula I

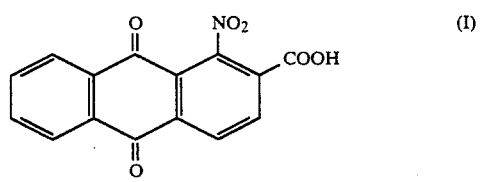

which comprises treating a 2-substituted 1-nitroanthraquinone of the general formula II

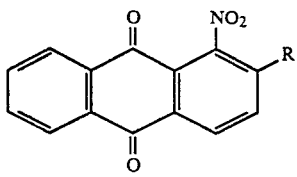

where R is —CH=CH—$R^1$ or —$CH_2$—CHO, where $R^1$ is $C_1$–$C_5$-dialkylamino or a cyclic 5- or 6-membered amine which may contain further hetero atoms, with an oxidizing agent free of heavy metal.

2. A process as claimed in claim 1, wherein the 2-substituted 1-nitroanthraquinone of the general formula II

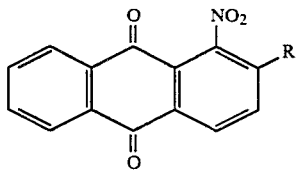

is obtained if R is —CH=CH—$R^1$ by reacting 2-methyl-1-nitroanthraquinone of the formula III

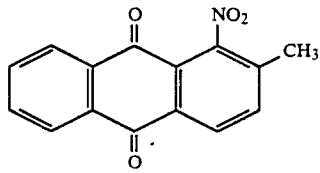

with a compound of the general formula IV

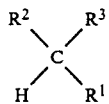

where $R^1$ is defined as in claim 1 and $R^2$ and $R^3$ are singly, and independently of each other, alkoxy or dialkylamino or together alkylenedioxy and if R is —$CH_2$—CHO the previously obtained compound where R is —CH=CH—$R^1$ is treated with a non-oxidizing mineral acid.

3. A 2-substituted 1-nitroanthraquinone of the general formula II

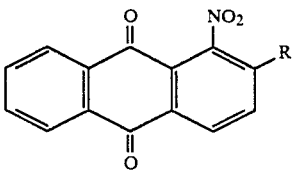

where R is —CH=CH—$R^1$ or —$CH_2$—CHO, where $R^1$ is $C_1$–$C_5$-dialkylamino or a cyclic 5- or 6-membered amine which may contain further hetero atoms.

* * * * *